US009157988B2

(12) United States Patent
Cho et al.

(10) Patent No.: US 9,157,988 B2
(45) Date of Patent: Oct. 13, 2015

(54) METHOD AND APPARATUS FOR ARRAY CAMERA PIXEL READOUT

(75) Inventors: Kwangbo Cho, San Jose, CA (US); Dongsoo Kim, San Jose, CA (US)

(73) Assignee: Semiconductor Components Industries, LLC, Phoenix, AZ (US)

( * ) Notice: Subject to any disclaimer, the term of this patent is extended or adjusted under 35 U.S.C. 154(b) by 621 days.

(21) Appl. No.: 13/371,312

(22) Filed: Feb. 10, 2012

(65) Prior Publication Data

US 2013/0027575 A1 Jan. 31, 2013

Related U.S. Application Data

(60) Provisional application No. 61/512,306, filed on Jul. 27, 2011.

(51) Int. Cl.

| | |
|---|---|
| ***H04N 5/225*** | (2006.01) |
| ***H04N 5/232*** | (2006.01) |
| ***G01S 7/486*** | (2006.01) |
| ***G01S 17/89*** | (2006.01) |
| *H04N 5/359* | (2011.01) |
| *H04N 5/3745* | (2011.01) |
| *H04N 13/02* | (2006.01) |

(52) U.S. Cl.

CPC ............... *G01S 7/4863* (2013.01); *G01S 17/89* (2013.01); *H04N 5/2258* (2013.01); *H04N 5/2327* (2013.01); *H04N 5/359* (2013.01); *H04N 5/37452* (2013.01); *H04N 13/0253* (2013.01)

(58) Field of Classification Search

CPC ....... G01S 17/89; G01S 7/4863; H04N 5/359; H04N 13/0253; H04N 5/37452; H04N 5/2258; H04N 5/2327; H04N 1/2137

USPC ....................... 348/230.1, 281, 292–294, 302

See application file for complete search history.

(56) References Cited

U.S. PATENT DOCUMENTS

| | | | | |
|---|---|---|---|---|
| 6,141,048 | A * | 10/2000 | Meyers | 348/294 |
| 7,262,799 | B2 * | 8/2007 | Suda | 348/280 |
| 2002/0113888 | A1 * | 8/2002 | Sonoda et al. | 348/315 |
| 2004/0041938 | A1 * | 3/2004 | Seo et al. | 348/340 |
| 2005/0001905 | A1 * | 1/2005 | Shinomiya | 348/207.99 |
| 2005/0046740 | A1 * | 3/2005 | Davis | 348/373 |
| 2010/0060746 | A9 * | 3/2010 | Olsen et al. | 348/222.1 |
| 2012/0012748 | A1 * | 1/2012 | Pain et al. | 250/332 |
| 2012/0188422 | A1 * | 7/2012 | Cho | 348/280 |

FOREIGN PATENT DOCUMENTS

| | | |
|---|---|---|
| EP | 0840502 | 5/1998 |

* cited by examiner

*Primary Examiner* — Hung Lam

(74) *Attorney, Agent, or Firm* — Treyz Law Group; Kendall P. Woodruff

(57) ABSTRACT

Imaging systems may include camera modules that include an array of image sensors. An image sensor may include multiple image pixel arrays arranged in rows and columns, multiple control circuits for operating the image pixels of that image sensor, and shared readout circuitry for reading out the image pixels of the image pixel arrays of that image sensor. Each control circuit may be operable to select rows of image pixels that extend across a row of image pixel arrays. Shared readout circuitry may include one or more line buffers configured to temporarily store image data captured by image pixels in the selected rows of image pixels. Shared readout circuitry may include selection circuitry configured to readout image data from groups of associated pixels located in separate image pixel arrays. An imaging system may include processing circuitry for processing the image data from each group of pixels.

18 Claims, 7 Drawing Sheets

METHOD AND APPARATUS FOR ARRAY CAMERA PIXEL READOUT

This application claims the benefit of provisional patent application No. 61/512,306, filed Jul. 27, 2011, which is hereby incorporated by reference herein in its entirety.

BACKGROUND

This relates generally to imaging systems, and more particularly, to imaging systems with multiple image sensors.

Image sensors are commonly used in imaging devices such as cellular telephones, cameras, and computers to capture images. In a typical arrangement, an imaging device is provided with a single image sensor with a single array of image sensor pixels and a single corresponding lens. Some imaging devices use arrays of image sensors and corresponding lenses to gather image data. This type of system, which is sometimes referred to as an array camera, may be used to extend depth of focus, increase output resolution through super-resolution processing, and capture depth information from a scene.

In a conventional array camera, each array of image sensor pixels is provided with control circuitry and pixel readout circuitry for operating that array of image sensor pixels. Image data from each array of image sensor pixels is therefore commonly readout separately and is often later combined using post-processing circuitry. This type of arrangement can require relatively large amounts of memory for storing full image frames from each array of image sensor pixels prior to combining the image frames. Providing sufficient memory for this type of image frame storage can be problematic.

It would therefore be desirable to be able to provide improved imaging systems with multiple arrays of image sensor pixels.

DETAILED DESCRIPTION

Digital camera modules are widely used in imaging systems in devices such as digital cameras, computers, cellular telephones, and other imaging devices. These imaging systems may include an image sensor array having one or more image sensors that gather incoming light to capture an image. An image sensor may include multiple arrays of image pixels. The image pixels in the image pixel arrays may include photosensitive elements such as photodiodes that convert the incoming light into digital data. Each array of image pixels may have any number of pixels (e.g., hundreds or thousands or more). A typical image pixel array may, for example, have hundreds, thousands, or millions of pixels (e.g., megapixels). An image sensor array may include multiple sets of multiple image pixel arrays. For example, an image sensor array may include four image sensors, each having a set of four image pixel arrays. An image sensor may include circuitry such as control circuitry and readout circuitry. Control circuitry and readout circuitry may be shared between one or more image pixel arrays of an image sensor.

Figure 1:
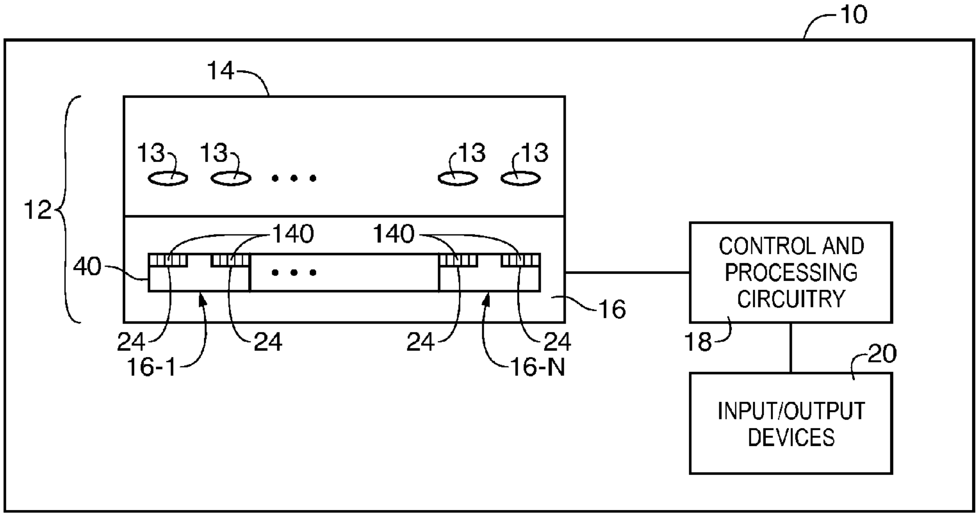
FIG. 1 is a diagram of an illustrative imaging system that contains a camera module with an array of lenses and an array of corresponding image pixel arrays in accordance with an embodiment of the present invention.

FIG. 1 is a diagram of an illustrative imaging system that uses an image sensor array to capture images. Imaging system 10 of FIG. 1 may be a portable imaging device such as a camera, a cellular telephone, a video camera, or other imaging device that captures digital image data. Camera module 12 may be used to convert incoming light into digital image data. Camera module 12 may include an array of lenses 14 and a corresponding array of image sensors 16. During image capture operations, light from a scene may be focused onto image pixel arrays 24 of image sensors 16-1, . . . 16-N using respective lenses 13 of lens array 14. Lens array 14 and image sensors 16 may be mounted in a common package and may provide image data to circuitry such as control and processing circuitry 18.

Control and processing circuitry 18 may include one or more integrated circuits (e.g., image processing circuits, microprocessors, storage devices such as random-access memory and non-volatile memory, etc.) and may be implemented using components that are separate from camera module 12 and/or that form part of camera module 12 (e.g., circuits that form part of an integrated circuit that includes image sensors 16 or an integrated circuit within module 12 that is associated with image sensors 16). Image data that has been captured by camera module 12 may be processed and stored using control and processing circuitry 18. Processed image data may, if desired, be provided to external equipment (e.g., a computer or other device) using wired and/or wireless communications paths coupled to control and processing circuitry 18.

There may be any suitable number of lenses 13 in lens array 14 and any suitable number of image pixel arrays 24 in image sensor array 16. Lens array 13 may, as an example, include N*M individual lenses arranged in an N×M two-dimensional array. The values of N and M may be equal or greater than two, may be equal to or greater than three, may exceed 10, or may have any other suitable values. Image sensor array 16 (sometimes referred to herein as an image sensor integrated circuit) may contain a corresponding N×M two-dimensional array of individual image pixel arrays 24. Each image sensor or image sensor array 16 may include one or more of image pixel arrays 24 of image pixels 140.

The image sensors may be formed on one or more separate semiconductor substrates. With one suitable arrangement, which is sometimes described herein as an example, four image sensors are formed on a common semiconductor substrate 40 (e.g., a common silicon image sensor integrated circuit die). Each image sensor in image sensor array 16 may include multiple arrays 24 of image pixels 140. Complementary metal-oxide-semiconductor (CMOS) technology or other image sensor integrated circuit technologies may be used in forming image sensor pixels 140. With one suitable arrangement, which is sometimes described herein as an example, each image sensor may include a set of four arrays 24 of image pixels 140. Each image sensor may be identical or there may be different types of image sensors in a given image sensor array integrated circuit. Each image sensor may be a Video Graphics Array (VGA) sensor with a resolution of 480×640 sensor pixels (as an example). Other types of sensor pixels may also be used for the image sensors if desired. For example, images sensors with greater than VGA resolution sensor (e.g., high-definition image sensors) or less than VGA resolution may be used, image sensor arrays in which the image sensors are not all identical may be used, etc.

Each image sensor of image sensor array 16 may include additional circuitry such as row control circuitry and readout circuitry. Row control circuitry and readout circuitry associated with each image sensor may be shared among one or more of the image pixel arrays 24 on that image sensor.

Imaging system 10 may provide a user with the ability to interact imaging device 10. User interactions may include inputting information. To implement these interactions, imaging device 10 may have input-output devices 20 such as keypads, virtual keypads, buttons, displays, or other suitable input-output components.

Figure 2:
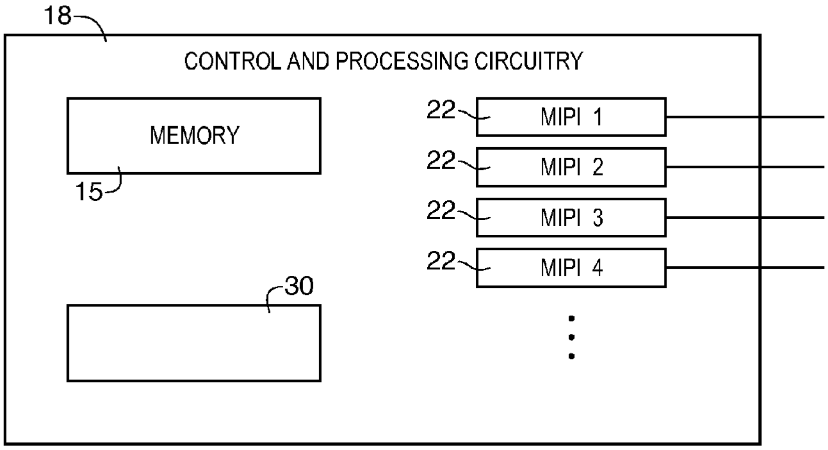
FIG. 2 is a diagram of an illustrative control and processing circuitry for operating a camera module having an array of image pixel arrays in accordance with an embodiment of the present invention.

As shown in FIG. 2, control and processing circuitry 18 of imaging device 10 may, if desired, include storage such as memory 15. Memory 15 may include volatile memory (e.g., static or dynamic random-access memory), non-volatile memory (e.g., flash memory), etc. Memory 15 may be configured to store image data, processed image data, spectral data, etc. resulting from image capture operations of system 10.

Control and processing circuitry 18 may include one or more serial interfaces such as serial interface circuits 22 for passing streams of image data from one or more corresponding image sensors of image sensor array 16. Each serial interface 22 (also called serial transports) may, for example, be a multi-lane serial transport or other high-speed serial interface such as a 4-lane Mobile Industry Processor Interface (MIPI) capable of transporting data from multiple arrays of image pixels to circuitry 18. Image sensor array 16 and some or all of circuitry 18 may, if desired, be formed from a single integrated circuit die. For example, serial interfaces 22 may be formed on a common integrated circuit die with image sensor array 16.

Control and processing circuitry 18 may include circuitry such as circuitry 30. Circuitry 30 may be configured to control input-output devices 20 and/or camera module 12 and to process image data captured using image sensor array 16. Circuitry 30 may include one or more integrated circuits mounted, for example, to a rigid or flexible printed circuit substrate.

The use of a camera module with an array of lenses and an array of corresponding image pixel arrays (i.e., an array camera) may allow images to be captured with increased depth of field because each image sensor in the array may be smaller than a conventional image sensor. The reduced image sensor size allows the focal length of each lens in the lens array to be reduced relative to that of a conventional single-lens configuration. Color cross-talk may also be reduced, because a single color filter can be used for each sub-array instead of using a conventional Bayer pattern or other multiple-color color filter array pattern. With a single color filter arrangement of this type, there is no opportunity or color information to bleed from one channel to another. As a result, signal-to-noise ratio and color fidelity may be improved.

The color filters that are used for the image sensor pixel arrays in the image sensors may, for example, be red filters, blue filters, and green filters. Each filter may form a color filter layer that covers the image sensor pixel array of a respective image sensor in the array. Other filters such as infrared-blocking filters, filters that block visible light while passing infrared light, ultraviolet-light blocking filters, white color filters, etc. may also be used. In an array with numerous image sensors, the image pixel arrays of some of the image sensors may have red filters, some may have blue color filters, some may have green color filers, some may have patterned color filters (e.g., Bayer pattern filters, etc.), some may have infrared-blocking filters, some may have ultraviolet light blocking filters, some may be visible-light-blocking-and-infrared-passing filters, etc.

The image sensor integrated circuit may have combinations of two or more, three or more, or four or more of these filters or may have filters of only one type. Control and processing circuitry 18 (e.g., processing circuitry integrated onto sensor array integrated circuit 16 and/or processing circuitry on one or more associated integrated circuits) can select which digital image data to use in constructing a final image for the user of device 10. For example, circuitry 18 may be used to blend image data from red, blue, and green sensors to produce full-color images, may be used to select an infrared-passing filter sensor when it is desired to produce infrared images, may be used to produce 3-dimensional images using data from two or more different sensors that have different vantage points when capturing a scene, etc.

In some modes of operation, all of image pixel arrays 24 on array 16 may be active (e.g., when capturing high-quality images). In other modes of operation (e.g., a low-power preview mode), only a subset of image pixel arrays 24 may be used. Other image pixel arrays may be inactivated to conserve power (e.g., their positive power supply voltage terminals may be taken to a ground voltage or other suitable power-down voltage and their control circuits may be inactivated or bypassed). In some modes of operations, all of the image pixel arrays 24 on array 16 may capture image data using a common integration (exposure) time or, if desired, some image pixel arrays 24 may capture image data using an integration time that is different from the integration time used to capture image data using other image pixel arrays 24. For example, image sensor array 16 may be used to capture high-dynamic-range images by capturing multiple images having different exposure times in order to accurately capture image data from low-light and bright-light regions of a scene.

Figure 3:
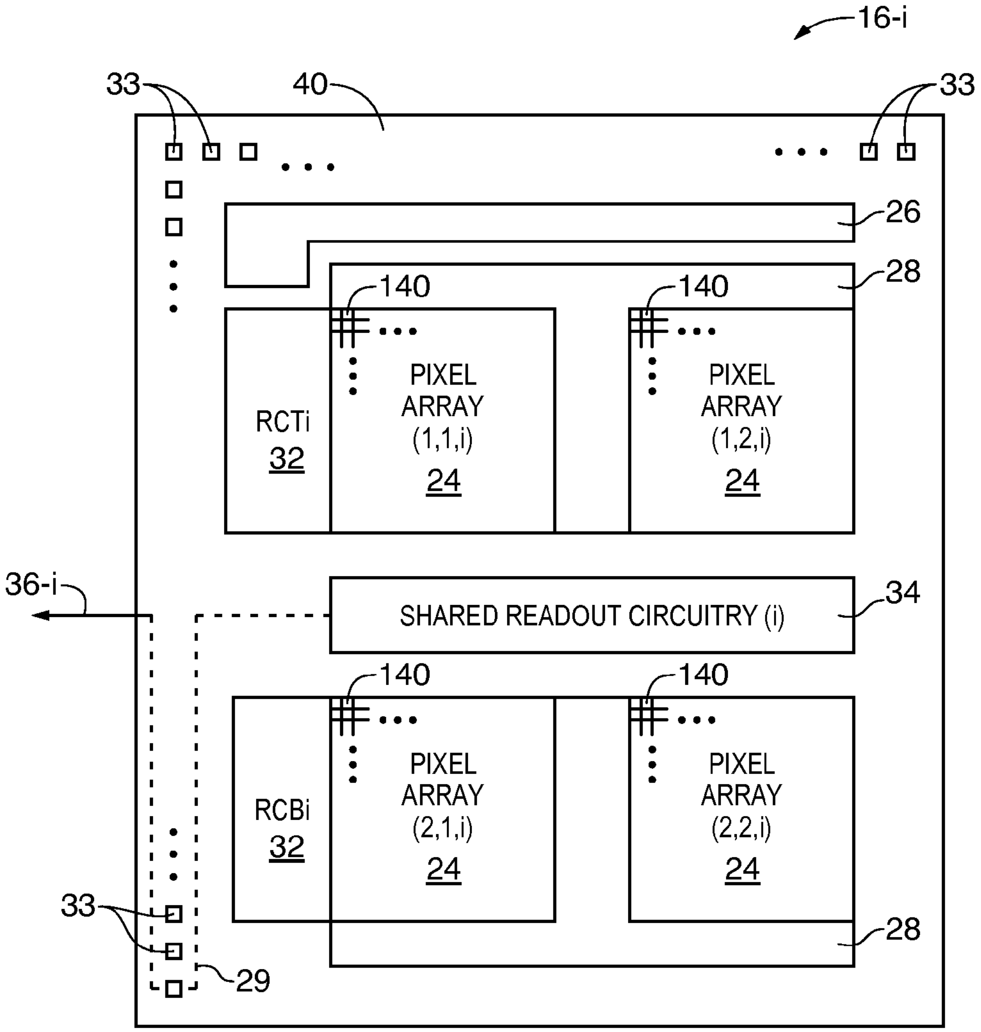
FIG. 3 is a diagram of an illustrative image sensor having multiple image sensor arrays of the type that may be used in the camera module of FIG. 1 in accordance with an embodiment of the present invention.

An illustrative image sensor of the type that may be used with camera module 12 of FIG. 1 is shown in FIG. 3. Image sensor 16-*i* of FIG. 3 may be formed on a substrate 40 such as a silicon semiconductor substrate may include one or more image sensors each having one or more image pixel arrays. As shown in FIG. 3 a given image sensor 16-*i* may include a set of multiple image pixel arrays 24 such as pixel array (1,1,i), pixel array (2,1,i), pixel array (1,2,i), and pixel array (2,2,i) on substrate 40. The image sensor of FIG. 3 has four image pixel arrays 24, but, in general, a given image sensor 16-*i* may have any suitable number of image arrays 24 of image pixels (e.g., two or more arrays, four or more arrays, ten or more arrays, 20 or more arrays, etc.). Each image pixel array 24 may include any number of image pixels 140. Image pixel arrays 24 may be arranged in rows of image pixel arrays and columns of image pixel arrays. As shown in FIG. 3, each row of image pixels arrays 24 may have an associated control circuit such as row control circuit 32 (also sometimes referred to as control circuitry or row control circuitry). In the example of FIG. 3, pixel array (1,1,i) and pixel array (1,2,i) may be formed along a first (e.g., top) row of image pixel arrays that are configured to be operated by top row control circuitry RCTi and pixel array (2,1) and pixel array (2,2) may be formed along a second (e.g., bottom) row of image pixel arrays that are configured to be operated by bottom row control circuitry RCBi.

Image data captured by the set of image pixel arrays 24 on a given image sensor 16-*i* may be read out using common readout circuitry such as shared readout circuit 34 (sometimes referred to as shared readout circuitry or as SRC(i) for image sensor 16-*i*). Shared readout circuitry 34 may include storage such as one or more line buffers for buffering image data from rows of image pixels in image pixel arrays 24, one or more column-select circuits for selecting columns of image pixels, or other circuitry such as bias circuitry (e.g., source follower load circuits), sample and hold circuitry, correlated double sampling (CDS) circuitry, amplifier circuitry, analog-to-digital (ADC) converter circuitry, data output circuitry, memory (e.g., buffer circuitry), address circuitry, etc.

Image sensor 16-*i* may include additional circuitry such as digital processing circuitry 26, dark-level correction circuitry 28, or other circuitry such as bias circuitry (e.g., source follower load circuits), sample and hold circuitry, correlated double sampling (CDS) circuitry, amplifier circuitry, analog-to-digital (ADC) converter circuitry, data output circuitry, memory (e.g., buffer circuitry), address circuitry, etc. Circuitry such as circuitry 26 and 28 may be formed entirely on substrate 40 or may be formed, in part, or entirely on an additional integrated circuit die.

Digital processing circuitry 26 may be configured to processes image data from image pixels 140. As examples, digital processing circuitry 26 may be configured to perform color corrections, white balance corrections, image combination operations, or any other suitable image processing operations. Dark-level correction circuitry 28 may include circuitry such as dark image pixels that form portions of image pixel arrays 24 and are prevented from receiving image light. Dark image pixels may form additional (light-shielded) rows and/or columns of image pixels that are coupled to row control circuitry 32 and readout circuitry 34 in substantially the same way that light receiving image pixels 140 are coupled to row control circuitry 32 and readout circuitry 34. In this way, dark signals may be captured by dark-level correction circuitry 28 that may be subtracted from image signals from image pixels 140. Dark-level correction circuitry 28 may provide dark signals to other circuitry on image sensor 16-*i* or dark-level correction circuitry 28 may include additional circuitry for performing analog subtraction of dark signals generated by dark image pixels from light-receiving image pixels 140.

Each image pixel array 24 may include at least some image pixels 140 that are configured to capture common portions of a scene with at least some image pixels 140 of another image pixel array 24 (e.g., corresponding image pixels in multiple image pixel arrays on image sensor 16-*i* or on multiple image sensors 16-*i* on image sensor array 16). Each image pixel array 24 may have an associated lens 13 in lens array 14 (FIG. 1) that is configured to project image light onto that image pixel array. Lens array 14 may be configured to project substantially the same portion of a scene onto each image pixel array 24 (of one or more image sensors 16-*i*) or, if desired, some lenses of lens array 14 may be configured to project partially overlapping or non-overlapping portions of a scene onto associated image pixel arrays 24.

As examples, in configurations in which each image pixel array receives image light through a single corresponding color filter, it may be desirable for image pixel arrays 24 to receive image light from substantially the same portion of a scene. However, in configurations in which it is desired that images captured by individual image pixel arrays 24 be combined to form a relatively higher resolution image (i.e., an output image having a higher pixel density than a given image pixel array), it may be desirable for each image pixel array 24 to receive image light from a portion of a scene that is shifted (e.g., by a fraction of a pixel) with respect to each other image pixel array 24. With one suitable configuration which is sometimes discussed herein as an example, each pixel of an image pixel array of image sensor array 16-*i* may have a corresponding pixel (e.g., a pixel in another image pixel array that receives image light from an overlapping portion of a scene) in every other image pixel array of image sensor array 16.

During image capture operations with image sensor 16-*i*, shared readout circuitry 34 may be configured to readout corresponding pixels from each image pixel array 24 in an order that allows image data from corresponding pixels to be processed together in small groups. For example, a group of overlapping pixels (e.g., one pixel from each of pixel array (1,1,i), pixel array (2,1,i), pixel array (1,2,i), and pixel array (2,2,i)) may be readout in order in a data stream prior to readout of a next group of overlapping pixels. In this way, image data from multiple image pixel arrays may be readout and processed (e.g., combined) without the need for image buffer storage capable of storing entire image frames.

A given image sensor 16-*i* may include a plurality of electrical contacts 33 for coupling the circuitry of image sensor 16-*i* to additional circuitry such as control and processing circuitry 18. Contacts 33 may, as examples, be bond pads formed on a common surface or opposing surface of substrate 40 with image pixels 140 or may be solder bumps formed on an opposing surface of substrate 40 from image pixels 140. Contacts 33 may be coupled (e.g., wire bonded, solder bumped, etc.) to additional circuitry such as control and processing circuitry 18 (FIG. 1). Input signals such as control signals may be routed to image sensor 16-*i* through bond pads 33. Data may be read out along a path such as output path 36-*i* from shared readout circuitry 34 of image sensor 16-*i* (e.g., using serial transports circuits 22) to control and processing circuitry 18. Some of electrical contacts 33 may be coupled to shared readout circuitry 34 (as indicated by dashed line 29) so that image data may be readout from shared readout circuitry 34 to circuitry 18 using electrical contacts 33 as a portion of output path 36-*i*).

As shown in FIG. 3, bond pads 33 may be formed along two adjacent edges (sides) of a substantially rectilinear image sensor 16-*i*. In this way, a single semiconductor wafer may be configured so that image sensors 16-*i* may be individually diced to form individual image sensors such as image sensor 16-*i* or may be diced in groups to form image sensor arrays such as image sensor array 16 of FIG. 4.

Figure 4:
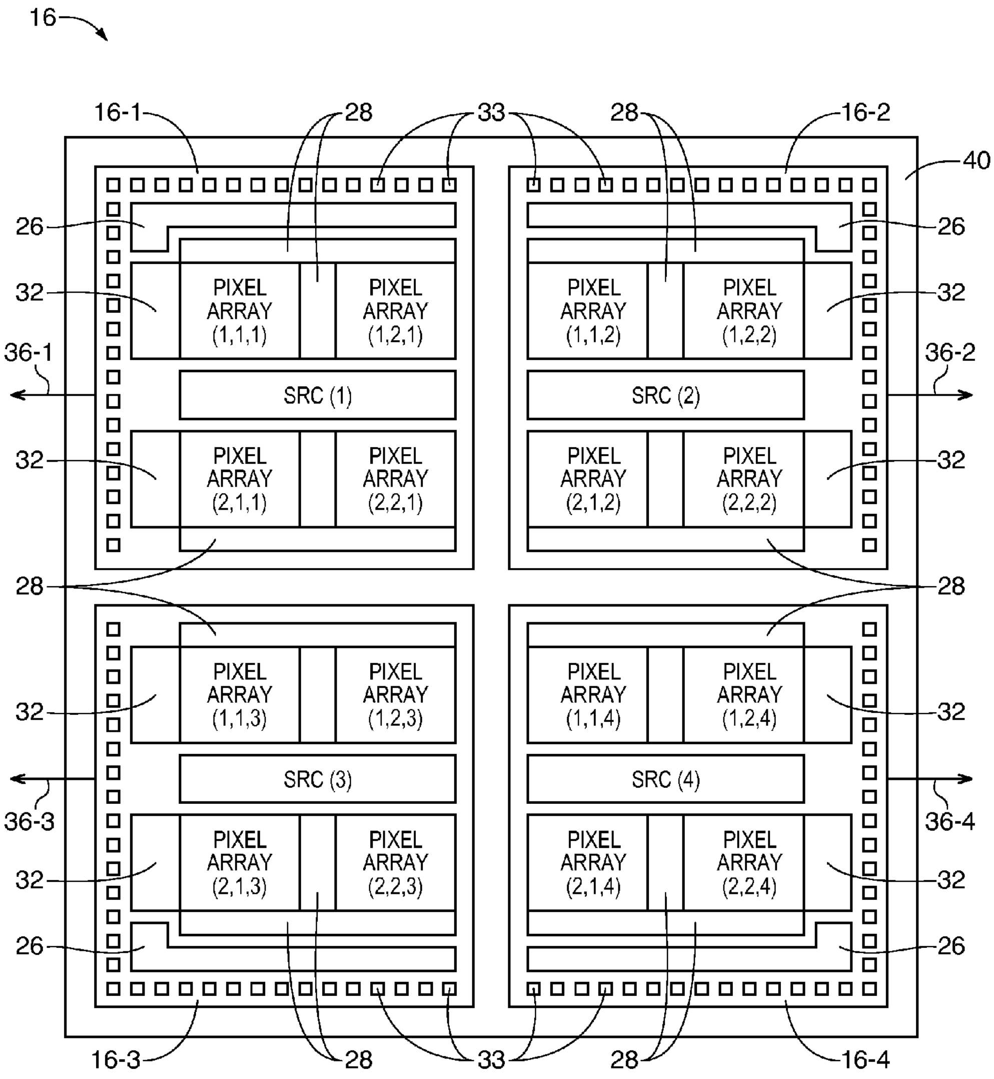
FIG. 4 is a diagram of an illustrative image sensor array of the type that may be used in the camera module of FIG. 1 in accordance with an embodiment of the present invention.

As shown in FIG. 4, substrate 40 may be diced so that image sensor array 16 includes multiple image sensors 16-*i* such as image sensors 16-1, 16-2, 16-3 and 16-4. Each image sensor 16-*i* may include an associated set of image pixel arrays 24. In the example of FIG. 4, each image sensor 16-*i* includes four image pixel arrays (e.g., PA(1,1,i), PA(1,2,i), PA(2,1,i) and PA(2,2,i)), where i represents an integer in the range from 1 through 4. This, however, is merely illustrative. If desired, i may be any suitable integer (i.e., image sensors array 16 may include any number of image sensors). Contacts 33 of each image sensor may be formed along two adjacent outer edges of each image sensor so that in configurations of the type shown in FIG. 4, contacts 33 are accessible along the outer perimeter of image sensor array 16. As described above in connection with FIG. 3, contacts 33 may be formed on a common surface of substrate 40 with image pixel arrays 24 or may be formed on an opposing surface of substrate 40.

Each image sensor of image sensor array 16 may have an associated output path. As shown in FIG. 4, image data captured by the image pixels of image sensor 16-1 may be readout along output path 36-1, image data captured by the image pixels of image sensor 16-2 may be readout along output path 36-2, image data captured by the image pixels of image sensor 16-3 may be readout along output path 36-3, and image data captured by the image pixels of image sensor 16-4 may be readout along output path 36-4. In this way, each image sensor 16 may be configured to have the capability of operating independently from other image sensors (e.g., for high-dynamic-range or time-of-flight image sensing).

Figure 5:
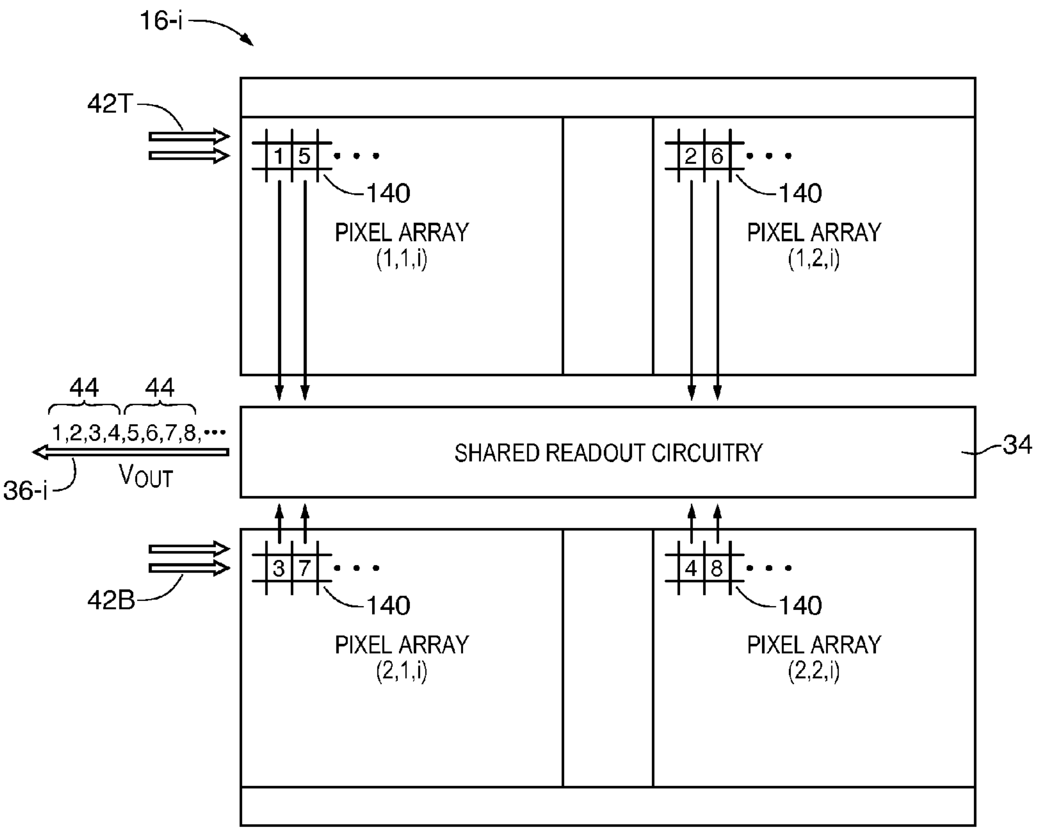
FIG. 5 is an illustrative diagram showing how ordered groups of image data from corresponding image pixels of multiple image pixel arrays may be readout using shared readout circuitry in accordance with an embodiment of the present invention.

FIG. 5 is a diagram showing how image data from overlapping pixels in multiple image pixel arrays may be read out in groups using shared readout circuitry 34. Rows of image pixels 140, each row extending across a first (e.g., top) row of image pixel arrays may be sequentially selected (as indicated by arrows 42T). Concurrently, rows of image pixels 140, each row extending across a second (e.g., bottom) row of image pixel arrays may be sequentially selected (as indicated by arrows 42B). Rows of image pixels may be selected by, for example, asserting a row select signal using row control circuitry RCTi and/or RCBi (FIG. 3). When a given row of image pixels 140 in each row of image pixel arrays is selected, image signals (image data) from image pixels in those rows may be read out using shared readout circuitry 34.

In the example of FIG. 5, pixels 1, 2, 3, and 4 may be overlapping pixels (e.g., pixels that receive image light from a common portion of a real-world scene). Similarly, pixels 5, 6, 7, and 8 may be overlapping pixels. Image signals Vout from image pixels such as image pixels 1, 2, 3, 4, 5, 6, 7, and 8 may be processed and output by shared readout circuitry 34 in groups 44 of overlapping pixels. In this way, groups 44 of corresponding image signals Vout may be provided to external circuitry such as circuitry 18 of FIG. 1. Providing image signals Vout to circuitry 18 in groups 44 of corresponding image signals may help reduce storage and computational power required by circuitry 18 to combine image pixel signals from multiple image pixel arrays to form combined output images.

Figure 6:
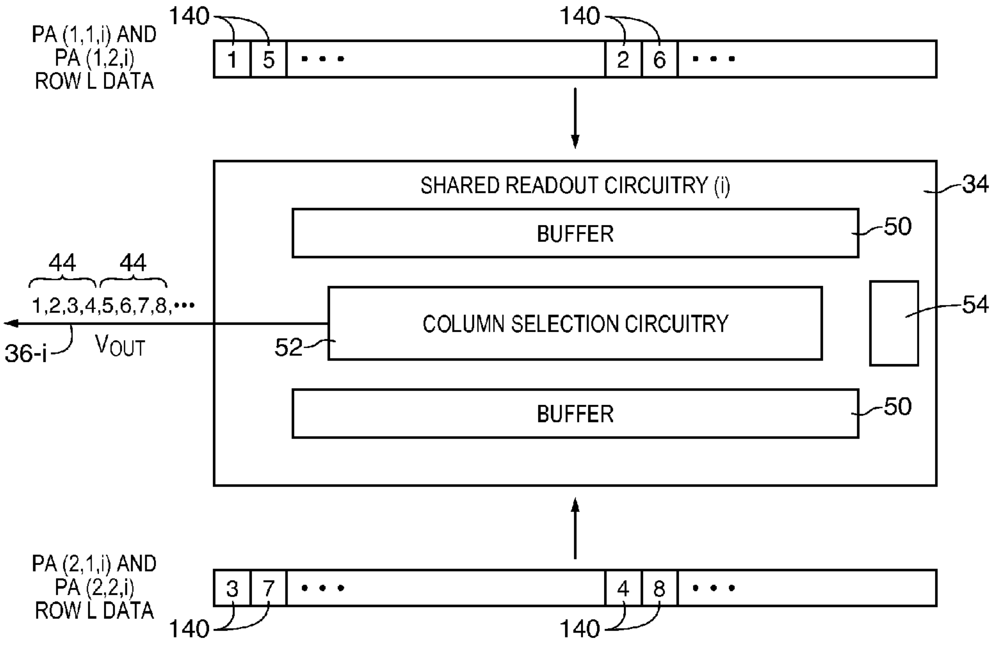
FIG. 6 is a diagram showing how corresponding rows of image pixels that extend across multiple image pixel arrays in rows of image pixel arrays may be temporarily stored in multiple line buffers in accordance with an embodiment of the present invention.

As shown in the schematic diagram of FIG. 6, shared readout circuitry 34 may include multiple buffers such as line buffers 50 that are configured to temporarily store image data from a corresponding row of image pixel arrays. Shared readout circuitry 34 may, for example, have a first line buffer 50 for storing image data from image pixels in a corresponding first (e.g., top) row of image pixel arrays and a second line buffer 50 for storing image data from image pixels in a corresponding second (e.g., bottom) row of image pixel arrays. A buffer 50 may provide sufficient storage to temporarily store image data from a row of image pixels that extends across a row of image pixel arrays.

Shared readout circuitry 34 may include selection circuitry such as column selection circuitry 52 for selectively reading out image signals Vout that are temporarily stored in line buffers 50. Shared readout circuitry 34 may include additional circuitry such as circuitry 54 for processing image signals from image pixels 140 prior to outputting image signals Vout. Circuitry 54 may include, for example, analog-to-digital (ADC) converter circuitry, sample and hold circuitry, correlated double sampling (CDS) circuitry, amplifier circuitry, data output circuitry, memory (e.g., buffer circuitry), or address circuitry.

During image capture and readout operations, image data from a row L of image pixels that spans image pixel arrays (1,1,i) and (1,2,i) in a row of image pixel arrays may be readout simultaneously from image pixels 140 and temporarily stored in one of line buffers 50. Concurrently, image data from a corresponding row L' of image pixels that spans image pixel arrays (2,1,i) and (2,2,i) in a row of image pixel arrays may be read simultaneously from image pixels 140 and temporarily stored in another one of line buffers 50. Column selection circuitry 52 may then be used to readout the stored image data from each pixel in an order that outputs image signals in groups 44 of corresponding image pixels. If desired, circuitry 54 may be used to process (e.g., convert to digital values) image signals before storing image signals in line buffers 50 or after storing image signals in line buffers 50 but before reading out image signals along path 36-*i*.

Figure 7:
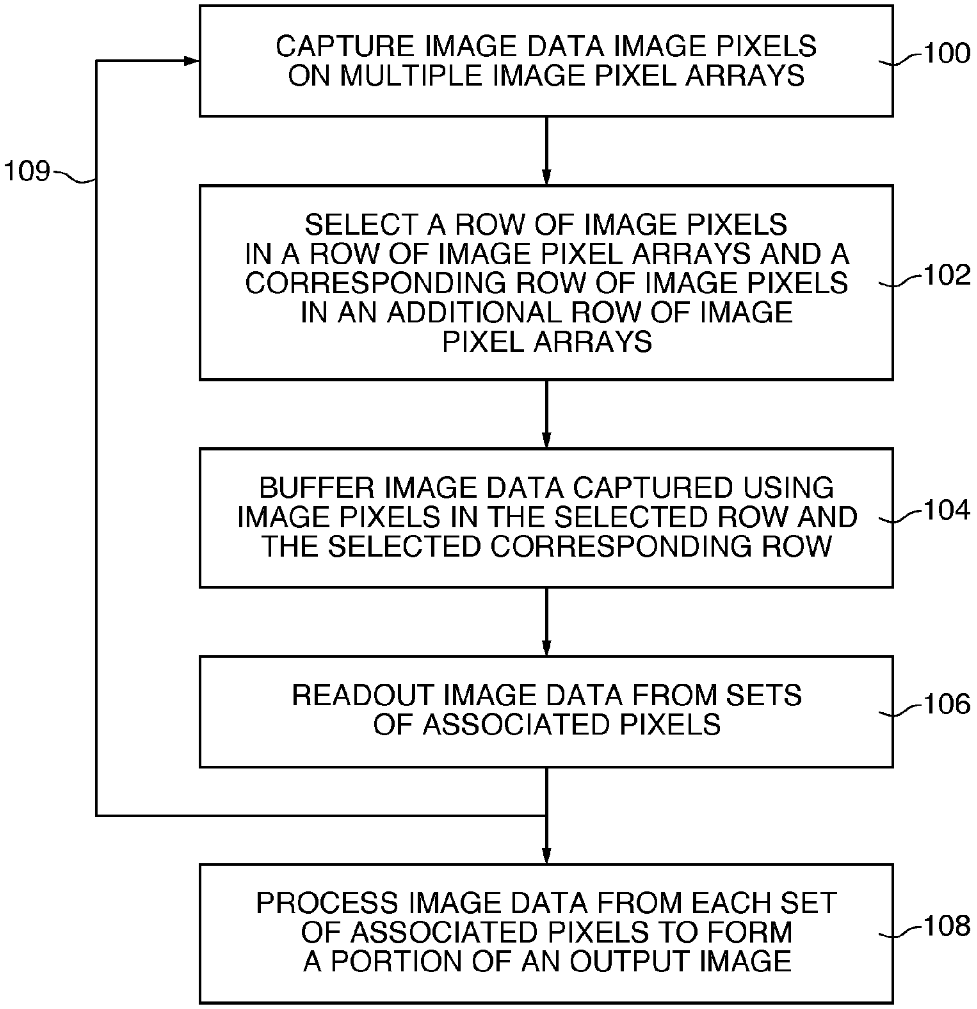
FIG. 7 is flow chart of illustrative steps involved in reading out image data from multiple image pixel arrays using shared control and readout circuitry in accordance with an embodiment of the present invention.

FIG. 7 is a flow chart illustrative of the steps involved in capturing and reading out image data from an image sensor having multiple image pixel arrays, control circuitry that is shared between some of the image pixel arrays, and readout circuitry that is shared between the image pixel arrays.

At step 100, image data may be captured using image pixels such as image pixels 140 (see, e.g., FIG. 1) in multiple image pixel arrays. The image pixel arrays may be formed on a single image sensor or multiple image sensors. Multiple image sensors may be formed on a single image sensor integrated circuit die or multiple image sensor integrated circuit die.

At step 102, a row of image pixels that spans multiple image pixel arrays and a corresponding row of image pixels that spans multiple additional image pixel arrays may be selected using, for example, row select circuitry RCTi and RCBi respectively of FIG. 3. The multiple image pixel arrays may form a row of image pixel arrays on an image sensor integrated circuit die. The multiple additional image pixel arrays may form an additional row of image pixel arrays on that image sensor integrated circuit die.

At step 104, image data that was captured using the image pixels in the selected row and the selected corresponding row may be read out and buffered in one or more corresponding buffers on the image sensor integrated circuit die.

At step 106, the buffered image data that was captured using the image pixels in the selected row and the selected corresponding row may be output in sets (groups) of associated (e.g., overlapping) pixels (i.e., the image data may be ordered for output such that the image data from each set of associated pixels may be output in sequence, without any intervening data). For example, in a configuration in which an image sensor includes four image pixel arrays that receive image light from a real-world scene, image data may be output in sets of four pixels (e.g., one pixel from each of the four image pixel arrays) that receive image light from a corresponding (e.g., overlapping, partially overlapping, or nearly overlapping) portion of a real-world scene.

At step 108, image data from each set of associated image pixels may be processed to form a portion of an output image. As examples, image data from four associated image pixels may be rendered as four image pixel signals in a relatively higher resolution image, may be rendered as four color image pixel signals in a color image, may be averaged to form one or more image pixel signals in an average image, may be selected from to form one or more image pixel signals in a high-dynamic-range image, or may be otherwise combined to form a portion of an output image. The processing of step 108 may be performed by circuitry (e.g., circuitry 26 of FIGS. 3 and 4) on the image sensor and/or other circuitry in imaging system 10 (e.g., circuitry 18 of FIG. 1).

As indicated by arrow 109, steps 100, 102, 104, and 106 may be repeated for each row of image pixels. The processing described in connection with step 108 (or other image processing) may be performed while image data from additional rows of image pixels in one or more rows of image pixel arrays is captured and/or readout using steps such as steps 100, 102, 104, and 106.

Figure 8:
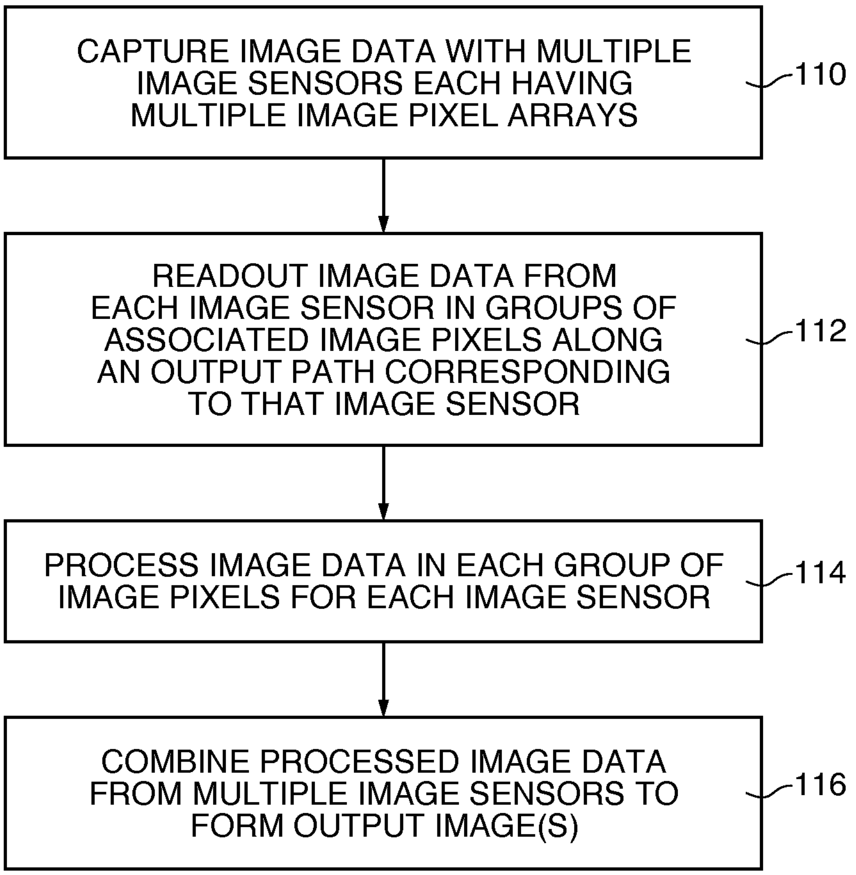
FIG. 8 is flow chart of illustrative steps involved in reading out image data from multiple image sensors each having multiple image pixel arrays using routing circuitry associated with each image sensor in accordance with an embodiment of the present invention.

FIG. 8 is a flow chart illustrative of the steps involved in capturing and reading out image data from multiple image sensors, each having multiple image pixel arrays, control circuitry that is shared between some of the image pixel arrays, and readout circuitry that is shared between the image pixel arrays.

At step 110, image data may be captured using image pixels such as image pixels 140 (see, e.g., FIG. 1) on multiple image sensors of an image sensor array, each image sensor having multiple image pixel arrays. The multiple image sensors may be formed on a common image sensor integrated circuit die or on multiple separate image sensor integrated circuit die.

At step 112, image data from image pixels on each image sensor may be read out in groups of associated image pixels (e.g., overlapping, partially overlapping, or nearly overlapping image pixels). Image data from each group (set) of associated image pixels on a given image sensor may be read out in sequence along an output data path such as paths 36-1, 36-2, 36-3, and 36-4 (FIG. 4) corresponding to that image sensor. Image data may be read out, for example, using a serial transport such as serial transports 22 of FIG. 2 to processing circuitry 18.

At step 114, image data in each group of associated image pixels may be processed using, as examples, circuitry (e.g., circuitry 26 of FIGS. 3 and 4) on the image sensor and/or other circuitry in imaging system 10 (e.g., circuitry 18 of FIG. 1). As examples, image data from four associated image pixels may be rendered as four image pixel signals in a relatively higher resolution image, may be rendered as four color image pixel signals in a color image, may be averaged to form one or more image pixel signals in an average image, may be selected from to form one or more image pixel signals in a high-dynamic-range image, or may be otherwise combined to form a portion of an output image.

At step 116, the processed (e.g., combined) image data described above in connection with step 114 from each image sensor may be combined with processed (e.g., combined) image data from one or more other image sensors to form one or more output images.

Various embodiments have been described illustrating apparatus and methods for capturing and reading out image data from multiple image pixel arrays using at least partially shared control and readout circuitry. An imaging system may include an image sensor array and an associated array of lenses that direct image light from a real-world scene onto image pixel arrays of each image sensor. Each image sensor may include multiple arrays of image pixels that convert the image light into image data. Each image sensor may include control circuitry such as row control circuitry that is configured to operate the image pixels in a row of image pixel arrays.

Each image sensor may include multiple rows of image pixel arrays that are operated by row control circuitry that is dedicated to that row of image pixel arrays. Each image sensor may include shared readout circuitry that is configured to readout image data from multiple image pixel arrays on the image sensor in groups of associated image pixels. Each group (set) of associated image pixels may be configured to receive image light from an associated portion of a real-world scene such as an overlapping portion of the scene. Image data may be readout in an order that groups image data from associated image pixels in order without any intervening data.

Each image sensor may be provided with a dedicated output path for reading out the image pixels of that image sensor. Image data from the image pixels of each image sensor may be readout along the output path associated with that image sensor and combined with image data from the image pixels of another image sensor. The image sensors of the image sensor array may be formed on a single, common image sensor integrated circuit die or may be formed on multiple separate image sensor integrated circuit die.

During operation of the imaging system, image data may be captured using image pixels in multiple image pixel arrays. The image pixel arrays may be formed on a single image sensor or multiple image sensors. Rows of image pixels that span multiple image pixel arrays and corresponding rows of image pixels that span multiple additional image pixel arrays may be simultaneously selected. Image data that was captured using the image pixels in the selected rows and the selected corresponding rows may be read out and buffered in turn into one or more corresponding buffers such as line buffers in the shared readout circuitry on the image sensor.

The buffered image data may be output in groups of associated pixels. Image data from each set of associated image pixels may be processed to form a portion of an output image. Output images may include relatively higher resolution images, may include color images, may include depth images, may include time-of-flight images, may include heat images, enhance depth-of-field images, or other processed images.

Image data from each group of associated image pixels on a given image sensor may be read out in sequence along an output data path that corresponds to that image sensor. Each data path may include a serial transport.

Processed or unprocessed image data from a given image sensor may be combined with processed or unprocessed image data image data from one or more other image sensors to form one or more output images.

The foregoing is merely illustrative of the principles of this invention which can be practiced in other embodiments.

What is claimed is:

1. An image sensor integrated circuit, comprising:

a substrate, a plurality of arrays of image pixels on the substrate;

first row control circuitry on the substrate that is configured to operate the image pixels of a first portion of the plurality of arrays of image pixels to capture image data;

second row control circuitry on the substrate that is configured to operate the image pixels of a second portion of the plurality of arrays of image pixels to capture additional image data;

a first line buffer for storing the image data from the image pixels of the first portion of the plurality of arrays of image pixels; and a second line buffer for storing the image data from the image pixels of the second portion of the plurality of arrays of image pixels, wherein the second line buffer is different from the first line buffer, and the first and second line buffers are respectively capable of storing the image data from the image pixels of the first and second portion of the plurality of arrays of image pixels simultaneously.

2. The image sensor integrated circuit defined in claim 1, further comprising:

shared readout circuitry configured to readout the image data from the image pixels of the first portion of the plurality of arrays of image pixels and the additional image data from the image pixels of the second portion of the plurality of arrays of image pixels, wherein the shared readout circuitry comprises the first and second line buffers.

3. The image sensor integrated circuit defined in claim 2 wherein the shared readout circuitry further comprises:

a selection circuit for selecting image data from the first and second line buffers.

4. The image sensor integrated circuit defined in claim 3 further comprising:

a plurality of electrical contacts on the substrate, wherein at least some of the plurality of electrical contacts are coupled to the shared readout circuitry.

5. The image sensor integrated circuit defined in claim 4, wherein the substrate has a surface, wherein the plurality of arrays of image pixels are formed on the surface and wherein the plurality of electrical contacts comprises a plurality of bond pads formed on the surface.

6. The image sensor integrated circuit defined in claim 5 wherein the electrical contacts are formed along at least two adjacent edges of the substrate on the surface.

7. The image sensor integrated circuit defined in claim 6 wherein at least some of the image pixels comprise complementary metal-oxide-semiconductor image sensor pixels.

8. The image sensor integrated circuit defined in claim 7 further comprising:

additional circuitry on the surface of the substrate that is configured to process the captured image data from the image pixels of at least some of the plurality of arrays of image pixels.

9. A camera module, comprising:

a substrate;

an array of image sensors on the substrate, each having first and second rows of image pixel arrays for capturing image data, first and second row control circuits, and shared readout circuitry on the substrate, wherein the shared readout circuitry of each image sensor includes separate first and second buffers for simultaneously storing a portion of the image data from the image pixels of the first and second rows of image pixel arrays respectively of that image sensor, wherein the first row control circuit of each image sensor is configured to operate the image pixels of the first row of image pixel arrays of that image sensor, and wherein the second row control circuit of each image sensor is configured to operate the image pixels of the second row of image pixel arrays of that image sensor.

10. The camera module defined in claim 9, further comprising:

an array of lenses, wherein each lens in the array of lenses is configured to focus image light onto a corresponding one of the image pixel arrays.

11. The camera module defined in claim 10 wherein the shared readout circuitry of each image sensor comprises:

a selection circuit for selecting image data from the first and second buffers.

12. The camera module defined in claim 11, further comprising processing circuitry configured to combine the image data captured by the image pixel arrays of the array of image sensors to form output images.

13. The camera module defined in claim 12 further comprising a plurality of serial transport circuits, wherein each serial transport circuit is configured to pass the image data from a corresponding one of the image sensors to the processing circuitry.

14. The camera module defined in claim 9, further comprising:

a plurality of electrical contacts on the substrate.

15. The camera module defined in claim 14, wherein the substrate has a surface and an outer perimeter, wherein the first and second rows of image pixel arrays are formed on the surface, wherein the plurality of electrical contacts are formed along the outer perimeter on the surface, and wherein the plurality of electrical contacts substantially surrounds the first and second rows of image pixel arrays.

16. A method of operating an imaging system having at least first, second, third, and fourth image pixel arrays and shared readout circuitry coupled to the image pixels of the first, second, third, and fourth image pixel arrays, the method comprising:

with the image pixels in the at least first, second, third, and fourth image pixel arrays, capturing image data; and with the shared readout circuitry, reading out the captured image data from a first image pixel of the first image pixel array followed by a corresponding first image pixel of the second image pixel array followed by a corresponding first image pixel of the third image pixel array followed by a corresponding first image pixel of the fourth image pixel array followed by a second image pixel of the first image pixel array followed by a corresponding second image pixel of the second image pixel array.

17. The method defined in claim 16 wherein the imaging system further comprises processing circuitry, the method further comprising:

with the processing circuitry, receiving the captured image data from the first image pixel of the first image pixel array and the corresponding first image pixel of the second image pixel array;

with the processing circuitry, combining the captured image data from the first image pixel of the first image pixel array and the corresponding first image pixel of the second image pixel array to form a first portion of an output image;

with the processing circuitry, receiving the captured image data from the second image pixel of the first image pixel array and the corresponding second image pixel of the second image pixel array from the shared readout circuitry; and with the processing circuitry, combining the captured image data from the second image pixel of the first image pixel array and the corresponding second image pixel of the second image pixel array to form a second portion of an output image.

18. The method defined in claim 17 wherein the imaging system further comprises processing circuitry, the method further comprising:

with the processing circuitry, receiving the captured image data from the first image pixel of the first image pixel array, the corresponding first image pixel of the second image pixel array, the corresponding first image pixel of the third image pixel array, and the corresponding first image pixel of the fourth image pixel array;

with the processing circuitry, combining the captured image data from the first image pixel of the first image pixel array, the corresponding first image pixel of the second image pixel array, the corresponding first image pixel of the third image pixel array, and the corresponding first image pixel of the fourth image pixel array to form a first portion of an output image;

with the processing circuitry, receiving the captured image data from the second image pixel of the first image pixel array and the corresponding second image pixel of the second image pixel array from the shared readout circuitry; and with the processing circuitry, combining at least the captured image data from the second image pixel of the first image pixel array and the corresponding second image pixel of the second image pixel array to form a second portion of an output image.

* * * * *